(12) United States Patent
Imajo et al.

(10) Patent No.: US 11,779,278 B2
(45) Date of Patent: Oct. 10, 2023

(54) BRAIN-MACHINE INTERFACE SYSTEM CAPABLE OF CHANGING AMOUNT OF COMMUNICATION DATA FROM INTERNAL DEVICE, AND CONTROL METHOD THEREFOR

(71) Applicants: NIHON KOHDEN CORPORATION, Tokyo (JP); OSAKA UNIVERSITY, Suita (JP); NATIONAL INSTITUTE OF INFORMATION AND COMMUNICATIONS TECHNOLOGY, Koganei (JP); SPChange, LLC., Yokohama (JP)

(72) Inventors: Kaoru Imajo, Tokyo (JP); Katsuyoshi Suzuki, Tokyo (JP); Masayuki Hirata, Suita (JP); Seiji Kameda, Suita (JP); Takafumi Suzuki, Koganei (JP); Hiroshi Ando, Koganei (JP); Takatsugu Kamata, Yokohama (JP)

(73) Assignees: NIHON KOHDEN CORPORATION, Tokyo (JP); OSAKA UNIVERSITY, Suita (JP); NATIONAL INSTITUTE OF INFORMATION AND COMMUNICATIONS TECHNOLOGY, Koganei (JP); SPChange, LLC., Yokohama (JP)

( * ) Notice: Subject to any disclaimer, the term of this patent is extended or adjusted under 35 U.S.C. 154(b) by 1044 days.

(21) Appl. No.: 16/484,922

(22) PCT Filed: Feb. 9, 2018

(86) PCT No.: PCT/JP2018/004561
§ 371 (c)(1),
(2) Date: Aug. 9, 2019

(87) PCT Pub. No.: WO2018/147407
PCT Pub. Date: Aug. 16, 2018

(65) Prior Publication Data
US 2020/0054284 A1 Feb. 20, 2020

(30) Foreign Application Priority Data
Feb. 10, 2017 (JP) ................................. 2017-023413

(51) Int. Cl.
*A61B 5/00* (2006.01)
*A61B 5/291* (2021.01)

(52) U.S. Cl.
CPC .......... *A61B 5/6868* (2013.01); *A61B 5/0006* (2013.01); *A61B 5/0031* (2013.01); *A61B 5/291* (2021.01)

(58) Field of Classification Search
CPC ..... A61B 5/6868; A61B 5/291; A61B 5/0006; A61B 5/0031
See application file for complete search history.

(56) References Cited

U.S. PATENT DOCUMENTS 6,230,049 B1\* 5/2001 Fischell ............... A61B 5/4094
600/544
2006/0049957 A1 3/2006 Surgenor et al.
(Continued)

FOREIGN PATENT DOCUMENTS

JP 2014-36862 A 2/2014
WO 2006/020794 A2 2/2006
(Continued)

OTHER PUBLICATIONS

Search Report dated Oct. 23, 2020 by the European Patent Office in counterpart European Patent Application No. 18751161.3.
(Continued)

*Primary Examiner* — Lindsey G Wehrheim
(74) *Attorney, Agent, or Firm* — Sughrue Mion, PLLC

(57) ABSTRACT

An internal device (1) is implanted in a living body (300). A control section (6) causes a communication section (5) to
(Continued)

wirelessly transmit data corresponding to electroencephalogram signals of the living body (300) which are detected through a group of N (N is 2 or more) electrodes, to an external device (200). When the communication section (5) receives a designation signal designating a group of M electrode(s) (2a), M being smaller than N, the communication section (5) is caused to transmit data corresponding to electroencephalogram signals of the living body (300) which are detected through the group of M electrode(s) (2a), to the external device (200) in real time.

14 Claims, 3 Drawing Sheets

(56) References Cited

U.S. PATENT DOCUMENTS

| | | |
|---|---|---|
| 2008/0021514 A1 | 1/2008 | Pless |
| 2014/0051044 A1 | 2/2014 | Badower et al. |
| 2014/0051960 A1 | 2/2014 | Badower et al. |
| 2014/0051961 A1 | 2/2014 | Badower et al. |
| 2015/0141789 A1 | 5/2015 | Knight et al. |
| 2015/0282730 A1 | 10/2015 | Knight et al. |
| 2015/0289980 A1 | 10/2015 | Hirata et al. |
| 2016/0166169 A1 | 6/2016 | Badower et al. |
| 2017/0049398 A1 | 2/2017 | Hirata et al. |
| 2018/0160930 A1 | 6/2018 | Knight et al. |

FOREIGN PATENT DOCUMENTS

| | | | |
|---|---|---|---|
| WO | 2006/041738 A2 | 4/2006 | |
| WO | WO-2008057365 A2 * | 5/2008 | ........... A61B 5/0476 |
| WO | WO-2009025863 A1 * | 2/2009 | ........... A61B 5/0476 |
| WO | 2009/089532 A1 | 7/2009 | |
| WO | 2012/063377 A1 | 5/2012 | |
| WO | 2015/114347 A1 | 8/2015 | |
| WO | 2015/164477 A1 | 10/2015 | |

OTHER PUBLICATIONS

Search Report dated May 1, 2018, issued by the International Searching Authority in International Application No. PCT/JP2018/004561 (PCT/ISA/210).

Written Opinion dated May 1, 2018, issued by the International Searching Authority in International Application No. PCT/JP2018/004561 (PCT/ISA/237.

Matsushita, Kojiro et al., "Development of an Implantable Wireless ECoG Recording Device—Performance Investigation of the first Prototype", May 27, 2012, The Japan Society of Mechanical Engineers, No. 12-3 Proceedings of the 2012 JSME Conference on Robotics and Mechatronics, 19 pages total.

Matsushita, Kojiro et al., "Development of an Implementable Wireless ECoG Recording Device—Performance Investigation of the second Prototype", Sep. 17, 2012, The 30th Annual Conference of the Robotics society of Japan DVD-ROM 2012, 16 pages total.

Takizawa, Kenichi et al., "Ultra wideband communications for wireless brain-machine interface with an ultra multi-channel neural recording system", Jul. 2, 2013, IEICE technical report, vol. 113, No. 117, 22 pages total.

* cited by examiner

BRAIN-MACHINE INTERFACE SYSTEM CAPABLE OF CHANGING AMOUNT OF COMMUNICATION DATA FROM INTERNAL DEVICE, AND CONTROL METHOD THEREFOR

TECHNICAL FIELD

The disclosure relates to a brain-machine interface (BMI) system configured by an internal device which is to be implanted in the living body, and an external device which is to be placed outside the living body.

BACKGROUND ART

An internal device acquires electroencephalograms functioning as a signal source to detect the brain activity, and transmits a signal which corresponds to the brain activity, or that which is obtained by processing the signal, to an external device. The external device operates in accordance with the signal received from the internal device. The internal device disclosed in Patent Literature 1 includes a plurality of electrodes which are to be implanted in the living body to detect electroencephalograms.

CITATION LIST

Patent Literature

Patent Literature 1: US Patent Application Publication No. 2006/0049957

SUMMARY OF INVENTION

Technical Problem

In order to know more correctly the condition of the brain, it is necessary to increase the number of electrodes (i.e., the number of channels) for detecting electroencephalograms. However, the larger the number of electrodes, the higher must be the rate of communication for transmitting data corresponding to acquired electroencephalogram signals to the external device in real time. A higher communication rate may cause restriction in the design of an implanted internal device.

Therefore, it is requested to enable a desired BMI control to be executed without increasing the communication rate.

Solution to Problem

A first mode for satisfying the request is an internal device of a brain-machine interface system, the internal device adapted to be implanted in a living body, the internal device comprising:

a communication section which wirelessly communicates with an external device; and a control section which controls the communication section, wherein the control section causes:

the communication section to transmit data corresponding to electroencephalogram signals of the living body which are detected through a group of N (N is 2 or more) electrodes, to the external device; and, when, after the transmission is performed, the communication section receives a designation signal designating a group of M electrode(s), M being smaller than N, the communication section to transmit data corresponding to electroencephalogram signals of the living body which are detected through the group of M electrode(s), to the external device in real time.

A second mode for satisfying the request is a method for controlling an internal device of a brain-machine interface system, the internal device adapted to be implanted in a living body, the method comprising:

wirelessly transmitting data corresponding to electroencephalogram signals of the living body which are detected through a group of N (N is 2 or more) electrodes to an external device;

after the wireless transmission is performed, wirelessly receiving a designation signal designating a group of M electrode(s), M being smaller than N; and wirelessly transmitting data corresponding to electroencephalogram signals of the living body which are detected through the group of M electrode(s) to the external device in real time.

According to the configurations of the first and second modes, data which are acquired through the group of N electrodes are first transmitted to the external device. The timing when the transmission is performed is set to, for example, a timing when the real time BMI control of the external device is not requested. Namely, sure delivery of data as many as possible to the external device takes precedence over the data transmission rate. Therefore, the communication section is not required to have a high data transmission capability.

Many data are supplied to the external device, and therefore a group of M electrode(s) which have a priority in order to perform a desired BMI control can be correctly identified. Furthermore, also the group of M electrode(s), M being smaller than N, is identified so as to match with the data transmission capability of the communication section. In a stage where the BMI control is actually performed, therefore, data corresponding to electroencephalogram signals which are acquired through the group of M electrode(s) are transmitted to the external device in real time. Consequently, a desired BMI control is enabled to be executed without increasing the communication rate.

A third mode for satisfying the request is an internal device of a brain-machine interface system, the internal device adapted to be implanted in a living body, the internal device comprising:

a data acquisition section;

a communication section which wirelessly communicates with an external device; and a control section which controls the communication section, wherein the control section causes:

the data acquisition section to acquire first data corresponding to electroencephalogram signals of the living body which are detected through N (N is 2 or more) electrodes, the first data having a first data amount;

the communication section to transmit the first data to the external device;

when, after the transmission is performed, the communication section receives a designation signal designating a second data amount which is smaller than the first data amount, the data acquisition section to acquire second data corresponding to electroencephalogram signals of the living body which are detected through the N electrodes, the second data having the second data amount; and the communication section to transmit the second data to the external device in real time.

A fourth mode for satisfying the request is a method for controlling an internal device of a brain-machine interface system, the internal device adapted to be implanted in a living body, the method comprising:

acquiring first data corresponding to electroencephalogram signals of the living body which are detected through a group of N (N is 2 or more) electrodes; the first data having a first data amount, and wirelessly transmitting the first data to an external device;

after the wireless transmission is performed, wirelessly receiving a designation signal designating a second data amount rather than the first data amount; and acquiring second data corresponding to electroencephalogram signals of the living body which are detected through the group of N electrodes, the second data having the second data amount, and wirelessly transmitting the second data to the external device in real time.

According to the configurations of the third and fourth modes, data which are acquired through the group of N electrodes, and the amount of which is relatively large are first transmitted to the external device. The timing when the transmission is performed is set to, for example, a timing when the real time BMI control of the external device is not requested. Namely, sure delivery of data as many as possible to the external device takes precedence over the data transmission rate. Therefore, the communication section is not required to have a high data transmission capability.

Many data are supplied to the external device, and therefore the second data amount which is required for performing a desired BMI control can be correctly identified. Moreover, the second data amount which is smaller than the first data amount is identified so as to match with the data transmission capability of the communication section. In a stage where the BMI control is actually performed, therefore, data of the second data amount which are acquired as they are through the group of N electrodes are transmitted to the external device in real time. Consequently, a desired BMI control is enabled to be executed without increasing the communication rate.

DESCRIPTION OF EMBODIMENTS

Hereinafter, embodiments will be described in detail with reference to the accompanying drawings.

Figure 1:
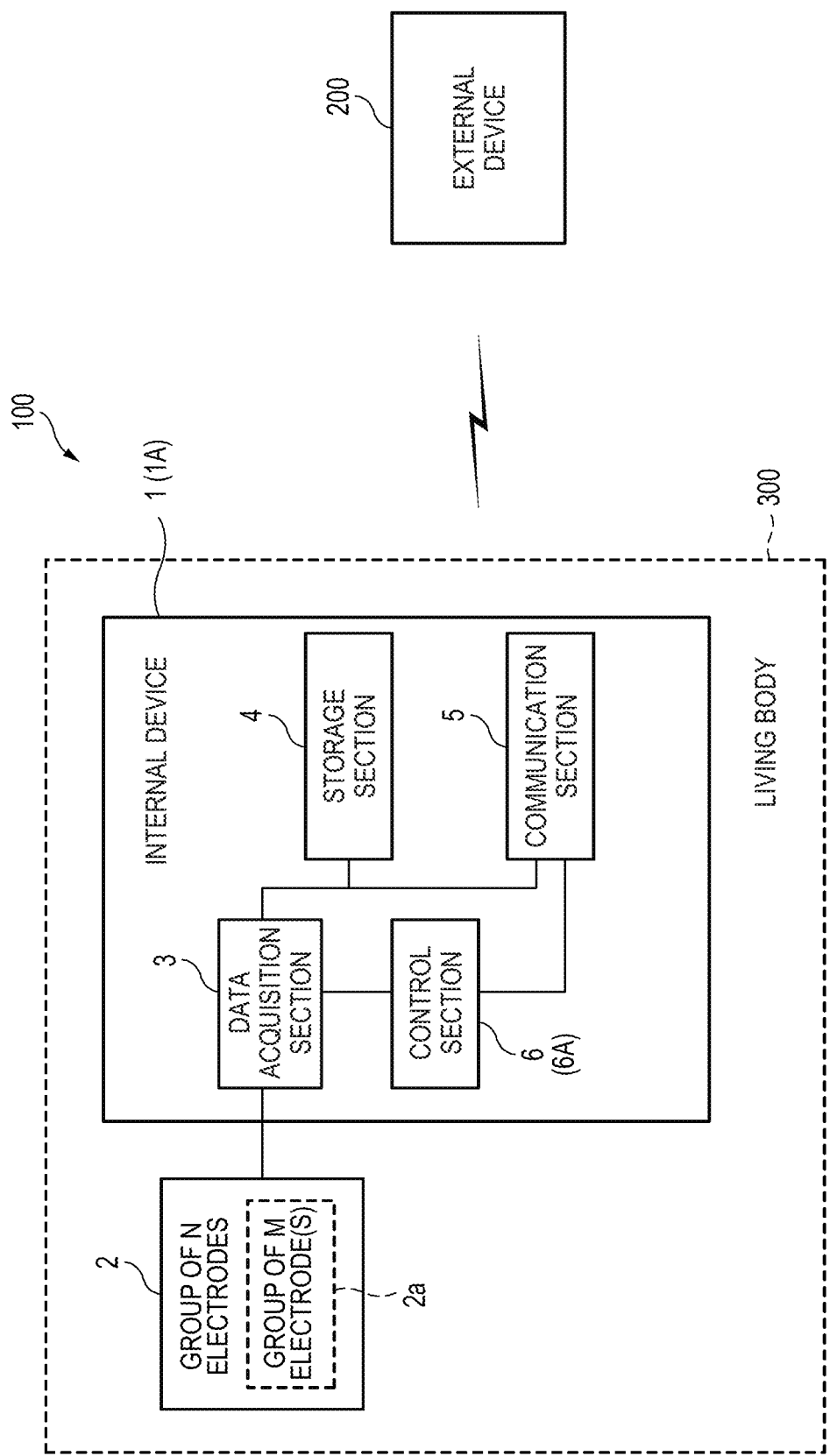
FIG. 1 is a diagram illustrating the functional configuration of a BMI system of a first embodiment.

FIG. 1 illustrates the functional configuration of a BMI system 100 of a first embodiment. The BMI system 100 may include an internal device 1 and an external device 200. The internal device 1 is configured so as to be used while being implanted in the living body 300 (specifically, the head). The external device 200 is configured so as to be used while being placed outside the living body 300.

The internal device 1 includes a group of N electrodes 2. In the following description, N is an integer of 2 or more. Each of the electrodes of the group of N electrodes 2 is configured so as to be attached to a predetermined place in the brain of the living body 300, and acquire an electroencephalogram signal in the place.

The internal device 1 may include a data acquisition section 3. The data acquisition section 3 may include an A/D converter. Electroencephalogram signals which are acquired through the group of N electrodes 2 are analog signals. The A/D converter is configured so as to convert the analog signals to digital data at a predetermined sampling rate and a predetermined resolution.

A sampling rate corresponds to the frequency at which a digital signal is acquired. When the frequency is 1 kHz, 1,000 digital data are acquired from an analog signal for one second. A resolution corresponds to the number of values which may be taken by digital data. When the resolution is 16 bits, the range of values which may be taken by the amplitude of an input analog signal is divided into 16 bits, and one of 2 to the 16th power values is allocated to the amplitude of the input analog signal.

The internal device 1 may include a communication section 5. The communication section 5 is communicably connected to the data acquisition section 3 and a storage section 4. The communication section 5 is configured so as to be able to execute wireless communication with the external device 200. The communication rate of the communication section 5 is set to be lower than that which is necessary for transmitting in real time digital data that are acquired through the group of N electrodes 2.

The internal device 1 may include a control section 6. The control section 6 is communicably connected to the data acquisition section 3 and the communication section 5. The control section 6 is configured so as to be able to control the operations of the data acquisition section 3 and the communication section 5.

The control section 6 is configured so as to cause the communication section 5 to wirelessly transmit all of digital data which correspond to electroencephalogram signals of the living body 300 that are detected through the group of N electrodes 2, and which are acquired by the data acquisition section 3, to the external device 200.

The control section 6 is configured so as to, when the communication section 5 wirelessly receives a designation signal designating a group of M electrode(s) 2a, M being smaller than N, cause the communication section 5 to wirelessly transmit digital data which correspond to electroencephalogram signals of the living body 300 that are detected through the group of M electrode(s) 2a, and which are acquired by the data acquisition section 3, to the external device 200 in real time.

The function of the control section 6 is realized from software (computer programs) executed by a cooperation of a processor and memory which are communicably connected to each other. Examples of the processor are a CPU, an MPU, and a GPU. Examples of the memory are a ROM and a RAM. However, the function of the control section 6 may be realized by a hardware resource such as an ASIC or an FPGA, or a combination of a hardware resource and software.

Next, a method for operating the thus configured internal device 1 will be described with reference to FIG. 2.

In a first time period, initially, a learning phase (S1) is performed. In the case where the living body 300 performs an operation of grasping the hand, thereby causing the external device 200 to execute a predetermined operation, for example, the living body 300 is made to perform a learning operation. Specifically, the living body 300 is made to actually grasp the hand, or caused to think about an operation of grasping the hand.

When the living body 300 performs a learning operation, an electroencephalogram corresponding to the learning operation is produced in the brain of the living body 300. The electroencephalogram is detected as N electroencephalogram signals by the group of N electrodes 2. The data acquisition section 3 acquires digital data corresponding to the N electroencephalogram signals (S2). In the case where the learning operation is performed for one second, for example, digital data corresponding to electroencephalogram signals for three seconds in total including before and after one second are acquired.

Thereafter, the control section 6 causes the communication section 5 to transmit all of the acquired digital data to the external device 200 (S4). The timing when the transmission is performed is a timing when the user inputs instructions to transmit, a predetermined time, a predetermined time interval, etc. The timing when the transmission is performed may be selected as a timing when real time monitoring of electroencephalogram signals is not necessary. The external device 200 receives data which are transmitted from the internal device 1 (S5).

The data transmission from the communication section 5 to the external device 200 is performed at a communication rate which is lower than the original transmission capability of the communication section 5, i.e., a value that is necessary for transmitting in real time data that are acquired through the group of N electrodes 2, to the external device 200. In the case where 128-channel electroencephalogram signals that are acquired through a group of 128 electrodes 2 are converted to digital data at a sampling rate of 1 kHz and a resolution of 16 bits, for example, a communication rate of about 2 Mbps is necessary (128 channels×16 bits×1 k samples/sec=2,048 kbits/sec=2 Mbps) for transmitting the data to the external device 200 in real time. When the communication rate of the communication section 5 is 0.5 Mbps, digital data corresponding to electroencephalogram signals for three seconds which are acquired by the data acquisition section 3 as described above are transmitted to the external device 200 with taking 12 seconds.

The external device 200 may be identical with or different from a device which receives the signals transmitted from the internal device 1, and which executes an operation based on the signals. For example, the external device 200 may be a device which receives the signals transmitted from the internal device 1, and which transmits a control signal that causes another external device to execute the operation based on the transmitted signals. Alternatively, the external device 200 may be a device dedicated for performing an analysis which will be described later.

The data which are received by the external device 200 are subjected to an analysis for reducing the amount of transmission data. In an actual BMI control, all of N electroencephalogram signals are not always required to have an accuracy which is similar to that in the learning process. The group of N electrodes 2 are arranged at relatively narrow intervals, where within the group N, there are electrodes that exhibit a strong correlation with the BMI control, but also electrodes which have no involvement in the BMI control. In the analysis, the group of M electrode(s) 2a (see FIG. 1) which have higher priority in the actual BMI control are specified (S6). M is an integer which is smaller than N. The value of M is adequately selected as a channel number corresponding to the data amount which is necessary in the BMI control.

In a second time period which is later than the first time period, an operating phase (S8) is performed. In the phase, the external device 200 is actually BMI-controlled by the living body 300. When the living body 300 grasps the hand, for example, a predetermined operation corresponding to the operation is executed by the external device 200.

Initially, a signal designating the group of M electrode(s) 2a which are selected based on the above-described analysis is transmitted from the external device 200. The signal is received by the communication section 5 of the internal device 1 (S7). When the signal is received by the communication section 5, the control section 6 changes the setting so that the data acquisition section 3 acquires only digital data corresponding to M electroencephalogram signals which are acquired through the group of M electrode(s) 2a (S9). The data acquisition section may acquire N electroencephalogram signals, but, when the acquisition is limited to the selected M signals, the power consumption can be reduced.

When the living body 300 operates in the same manner as the above-described learning operation, an electroencephalogram corresponding to the learning operation is produced in the brain of the living body 300. In the operating phase (S8), therefore, the data acquisition section 3 acquires digital data corresponding to electroencephalogram signals based on the above-described setting (S9). The control section 6 causes the communication section 5 to transmit in real time the digital data which are acquired by the data acquisition section 3, to the external device 200 (S10). While repeating the operations of S9 and S10 (S12), the external device 200 executes in real time a predetermined operation based on the data which are transmitted from the communication section 5 (S11).

The group of M electrode(s) 2a are selected so that a desired BMI control can be executed. Moreover, the group of M electrode(s) 2a are selected so that the communication section 5 can transmit in real time data corresponding to electroencephalogram signals which are acquired through the electrode group. Therefore, a real time BMI control of the external device 200 which corresponds to the operation of the living body 300 is realized.

According to the operating method in which the thus configured internal device 1 is used, in the learning phase, data which are acquired through the group of N electrodes 2, and the amount of which is relatively large are transmitted to the external device 200. In the phase, sure delivery of data as many as possible to the external device 200 takes precedence over the data transmission rate. Therefore, the communication section 5 is not required to have a high data transmission capability.

When many data are supplied to the external device 200, the group of M electrode(s) 2a which has a priority in order to perform a desired BMI control can be correctly identified. Furthermore, the group of M electrode(s) 2a the number of which is smaller than N are identified so as to match with the data transmission capability of the communication section 5. In the operating phase, therefore, data corresponding to electroencephalogram signals which are acquired through the group of M electrode(s) 2a are transmitted in real time to the external device 200. This enables a desired BMI control to be executed without increasing the communication rate.

In order to perform the above-described learning phase, the system may include the storage section 4 as illustrated in FIG. 1. The storage section 4 is communicably connected to the data acquisition section 3. The storage section 4 is configured so as to be able to store digital data which are acquired by the data acquisition section 3.

The control section 6 is communicably connected to the storage section 4. As illustrated in FIG. 2, prior to the above-described transmission (S4), the control section 6 causes the storage section 4 to store the digital data which are acquired by the data acquisition section 3 (S3).

Figure 2:
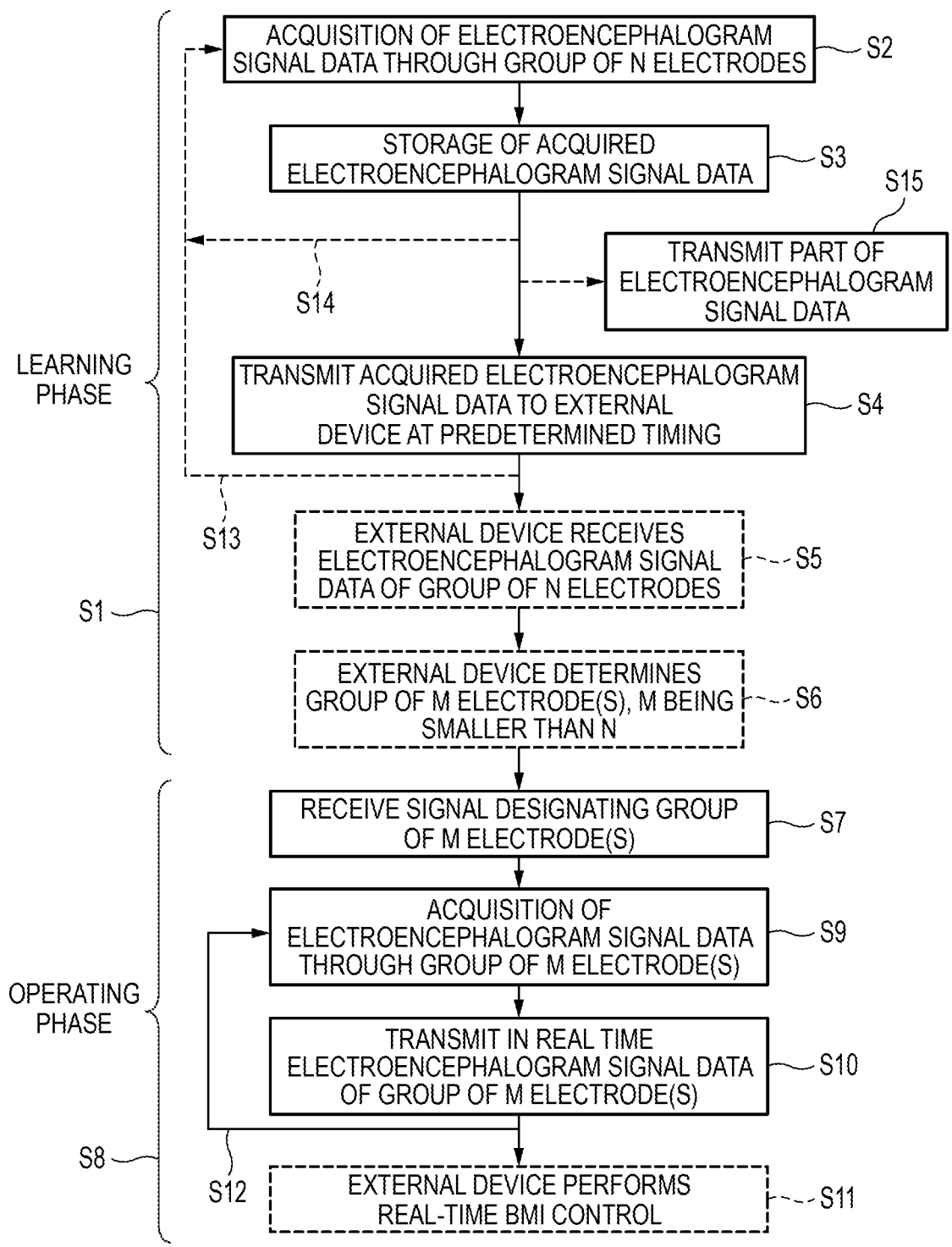
FIG. 2 is a flowchart illustrating the operation of the BMI system.

As illustrated by the arrow of the broken line in FIG. 2, the control section 6 may repeat as required steps S2 to S4 through step S3 (S13). Namely, the learning operation by the living body 300, the acquisition (S2) and storage (S3) of digital data corresponding to the N electroencephalogram signals which are acquired through the group of N electrodes 2, and the transmission (S4) of the digital data to the external device 200 are repeated until desired electroencephalogram signal data that are necessary for the analysis in the learning phase are accumulated. According to the configuration, although the frequency of communications between the communication section 5 and the external device 200 is increased, the necessity of ensuring a large capacity in the storage section 4 is reduced. Since the system includes the storage section, the digital data can be transmitted at an arbitrary timing. Therefore, the communication section is not required to have a high data transmission capability not only in the operating phase but also in the learning phase. Consequently, effects of reduction of the power consumption and suppression of heat generation are expected also in the learning phase. Moreover, the area of the communication section tends to be increased in accordance with the level of the data transmission capability. When the data transmission capability in both the learning and operating phases is suppressed to a low level, therefore, the area of the communication section can be reduced.

Prior to the above-described transmission (S4), alternatively, the control section 6 may repeat as required the steps S2 and S3 (S14). Namely, the learning operation by the living body 300, and the acquisition (S2) and storage (S3) of digital data corresponding to the N electroencephalogram signals which are acquired through the group of N electrodes 2 are repeated until desired electroencephalogram signal data that are necessary for the analysis in the learning phase are accumulated. Then, the data which are accumulated in the storage section 4 are collectively transmitted to the external device 200 (S4). According to the configuration, the frequency of communications between the communication section 5 and the external device 200 can be reduced. Also in this operating method, the system includes the storage section, and therefore the communication section is not required to have a high data transmission capability even in the learning phase. Consequently, effects of reduction of the power consumption, suppression of heat generation, and reduction in size of the communication section are expected.

Alternatively, data of a group of arbitrary electrode(s) the number of which is smaller than N may be transmitted in real time to the external device 200. In the case where data of one electrode are transmitted in real time to the external device 200, for example, the learning operation by the living body 300, the acquisition (S2) of digital data corresponding to one electroencephalogram signal which is acquired through one certain electrode, and the real time transmission (S4) of the digital data to the external device 200 are repeated until desired electroencephalogram signal data that are necessary for the analysis in the learning phase on the one certain electrode are accumulated. When this process is repeated on N electrodes, N electroencephalogram signal data that are necessary for the analysis in the learning phase can be acquired (S5). According to the configuration, although the same learning operation must be repeated many times, the storage section 4 illustrated in FIG. 1 and step S3 illustrated in FIG. 2 are not necessary. When the number of electrode data which are transmitted at one time is increased in accordance with the transmission capability of the communication section 5, the time period of the learning phase can be shortened.

Moreover, a configuration where the communication section 5 can transmit in real time data of all of the group of N electrodes 2 to the external device 200 may be possible. Also in this case, the storage section 4 illustrated in FIG. 1 and step S3 illustrated in FIG. 2 are not necessary. Namely, the learning operation by the living body 300, the acquisition (S2) of digital data corresponding to N electroencephalogram signals which are acquired through the group of N electrodes 2, and the real time transmission (S4) of the digital data to the external device 200 are repeated until desired electroencephalogram signal data that are necessary for the analysis in the learning phase are accumulated. Although the power consumption in the learning phase cannot be reduced, an effect of reduction of the power consumption due to reduction of the number of electrode data to be transmitted can be obtained in the operating phase.

Prior to the above-described transmission (S4), moreover, the control section 6 may cause the communication section 5 to transmit a part of data stored in the storage section 4 to the external device 200 (S15). Such a process may be performed in order to check whether the internal device 1 normally operates or not. When the communication section 5 receives instructions from the external device 200, such a process may be performed.

In the embodiment, the control section 6 causes all of data corresponding to N electroencephalogram signals which are acquired in the learning phase by the data acquisition section 3, to be transmitted to the external device 200. However, it is not always necessary to transmit all of data corresponding to N electroencephalogram signals. It is requested that the number of electroencephalogram signals which are transmitted in the learning phase is larger than that of electroencephalogram signals which are transmitted in the operating phase.

Figure 3:
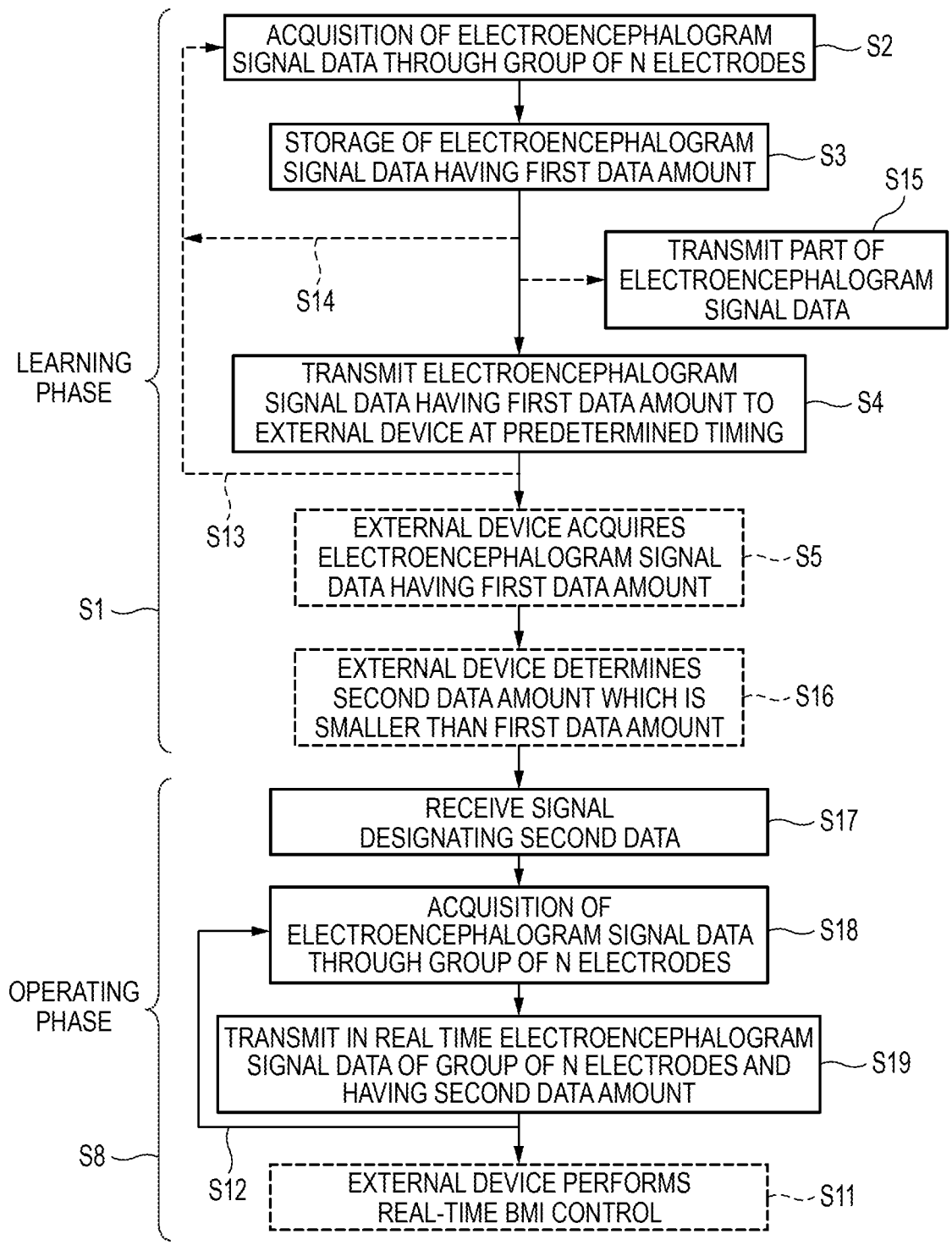
FIG. 3 is a flowchart illustrating the operation of a BMI system of a second embodiment.

Next, an internal device 1A of a second embodiment will be described with reference to FIG. 3. The components identical or equivalent to those of the internal device 1 of the first embodiment are denoted by the same reference numerals, and repeated description will be omitted.

As illustrated in FIG. 1, the internal device 1A may include a control section 6A. The control section 6A is communicably connected to the data acquisition section 3 and the communication section 5. The control section 6A is configured so as to be able to control the operations of the data acquisition section 3 and the communication section 5.

The control section 6A is configured so as to cause the communication section 5 to wirelessly transmit all of digital data which correspond to electroencephalogram signals of the living body 300 that are detected through the group of N electrodes 2, and which are acquired by the data acquisition section 3, to the external device 200. Namely, digital data having a first data amount are transmitted to the external device 200.

The control section 6A is configured so as to, when the communication section 5 wirelessly receives a designation signal designating a second data amount which is smaller than the first data amount, cause the data acquisition section 3 to acquire digital data which correspond to electroencephalogram signals of the living body 300 that are detected through the group of N electrodes 2, and which have a second data amount.

Specifically, the control section 6A lowers the data sampling rate, thereby reducing the data amount of digital data to be acquired. Alternatively, the control section 6A lowers the data resolution, thereby reducing the data amount of digital data to be acquired. In order to reduce the amount of digital data to be acquired, the control section 6A may lower both the sampling rate and the resolution. An example of the lowering of the resolution is lowering from 16 bits to 8 bits. The reductions of the sampling rate and the resolution may be performed through a hardware process or a software process.

The control section 6A is configured so as to cause the communication section 5 to wirelessly transmit the digital data which are acquired as described above, to the external device 200 in real time.

The function of the control section 6A is realized from software executed by a cooperation of a processor and memory which are communicably connected to each other. Examples of the processor are a CPU and an MPU. An example of the memory is a RAM. However, the function of the control section 6 may be realized by hardware such as an ASIC or an FPGA, or a combination of hardware and software.

Next, a method for operating the thus configured internal device 1A will be described with reference to FIG. 3. The components identical to those of the operating method illustrated in FIG. 2 are denoted by the same reference numerals, and repeated description will be omitted.

In a first time period, the learning phase (S1) is performed. When the living body 300 performs a learning operation, an electroencephalogram corresponding to the learning operation is produced in the brain of the living body 300. The electroencephalogram is detected as N electroencephalogram signals by the group of N electrodes 2. The data acquisition section 3 acquires digital data which correspond to the N electroencephalogram signals, and which have the first data amount (S2). In the case where the learning operation is performed for one second, for example, digital data corresponding to electroencephalogram signals for three seconds in total including before and after one second are acquired. The control section 6A causes the storage section 4 to store the digital data (S3).

Thereafter, the control section 6A causes the communication section 5 to transmit all of the acquired digital data to the external device 200 (S4). The data transmission from the communication section 5 to the external device 200 is performed at a communication rate which is lower than the original transmission capability of the communication section 5, i.e., a value that is necessary for transmitting in real time data that are acquired through the group of N electrodes 2, to the external device 200. The external device 200 receives the data which are transmitted from the internal device 1 (S5).

The data which are received by the external device 200 are subjected to an analysis for reducing the amount of transmission data. In the analysis, a second data amount at which a realistic BMI control can be performed without exceeding the real time data transmission capability of the communication section 5 is identified (S16).

In the second time period which is later than the first time period, the operating phase (S8) is performed. A signal designating the second data amount which is selected based on the above-described analysis is transmitted from the external device 200. The signal is received by the communication section 5 of the internal device 1A (S17). When the signal is received by the communication section 5, the control section 6A changes the setting so that digital data having the second data amount can be transmitted.

For example, the control section 6A lowers at least one of the data sampling rate and the resolution. In the case where the communication rate which is necessary for transmitting in real time digital data having the first data amount that are acquired at a first sampling rate and a first resolution through the group of N electrodes 2 is 2 Mbps, and the real time data transmission capability of the communication section 5 is 0.5 Mbps, for example, the control section 6A can reduce the amount of digital data which are acquired in the following manner, to the second data amount:

the first sampling rate is changed to a second sampling rate which is one quarter of the first sampling rate;
the first resolution is changed to a second resolution which is one quarter of the first resolution; and
the first sampling rate is changed to the second sampling rate which is one half of the first sampling rate, and the first resolution is changed to the second resolution which is one half of the first resolution (when the amount of the transmitted data is reduced to one quarter, the combination of the reduction amount of the sampling rate and that of the resolution can be adequately determined).

Data which are acquired at the first resolution through a hardware process may be converted to those of the second resolution through a subsequent software process. The resolution and the sampling rate may be changed for each of the electrodes.

When the living body 300 operates in the same manner as the above-described learning operation, an electroencephalogram corresponding to the operation is produced in the brain of the living body 300. The data acquisition section 3 acquires digital data having the second data amount through the group of N electrodes 2 (S18). The control section 6A causes the communication section 5 to transmit in real time the digital data which are acquired by the data acquisition section 3, to the external device 200 (S19). While repeating the operations of S18 and S19 (S12), the external device 200 executes in real time a predetermined operation based on the data which are transmitted from the communication section 5 (S11).

The second data amount is selected so that a desired BMI control can be executed. Moreover, the second data amount is selected so that the communication section 5 can transmit in real time the acquired digital data. Therefore, a real time BMI control of the external device 200 which corresponds to the operation of the living body 300 is realized.

According to the operating method in which the thus configured internal device 1A is used, in the learning phase, data which are acquired through the group of N electrodes 2, and which have the first date amount that is relatively large are once stored in the storage section 4. The stored data are then transmitted to the external device 200. In the phase, sure delivery of data as many as possible to the external device 200 takes precedence over the data transmission rate. Therefore, the communication section 5 is not required to have a high data transmission capability.

The operating method in the first embodiment in which the storage section 4 is not required in learning phase can be applied also to the second embodiment.

When many data are supplied to the external device 200, the second data amount which is necessary in order to perform a desired BMI control can be correctly identified. Furthermore, the second data amount is identified so as to match with the data transmission capability of the communication section 5. In the operating phase, therefore, data corresponding to electroencephalogram signals which are acquired through the group of N electrodes 2 are transmitted in real time as they are to the external device 200. This enables a desired BMI control to be executed without increasing the communication rate.

In the embodiment, the control section 6A causes all of digital data which are acquired in the learning phase by the data acquisition section 3, and which have the first data amount, to be transmitted to the external device 200. However, it is not always necessarily to transmit all of data having the first data amount. It is requested that the amount of data which are transmitted in the learning phase is larger than that of data which are transmitted in the operating phase.

The above-described embodiments are mere examples for facilitating understanding of the disclosure. The configurations of the embodiments may be adequately changed or improved without departing from the spirit of the presently disclosed subject matter. When the first and second embodiments are combined with each other, for example, the sampling rate and resolution of data which are acquired by a group of M electrode(s), M being smaller than N, may be lowered, and the amount of transmitted data may be further reduced.

The disclosure of Japanese Patent Application No. 2017-023413 filed Feb. 10, 2017 is incorporated herein by reference as constituents of the description of the application.

The invention claimed is:

1. An internal device of a brain-machine interface system, the internal device adapted to be implanted in a living body, the internal device comprising:
    a communication section which wirelessly communicates with an external device; and
    a control section which controls the communication section, wherein
    the control section causes:
    the communication section to transmit first data corresponding to electroencephalogram signals of the living body for causing the external device to execute a predetermined operation which are detected through a group of N (N is 2 or more) electrodes, to the external device at a communication rate which is lower than a value that is necessary for transmitting in real time; and,
    when, after the transmission of the first data is performed, the communication section receives, from the external device, a designation signal designating a group of M electrode(s), M being smaller than N, the communication section to transmit second data corresponding to electroencephalogram signals of the living body for causing the external device to execute the predetermined operation which are detected through the group of M electrode(s), to the external device in real time.

2. The internal device according to claim 1, further comprising:
    a storage section, wherein
    prior to the transmission of the first data, the control section causes the storage section to repeatedly store the first data.

3. The internal device according to claim 1, wherein
    prior to the transmission of the first data, the control section causes the communication section to transmit a part of the first data to the external device.

4. The internal device according to claim 1, wherein
    the control section causes the communication section to transmit the first data to the external device when the living body performs a learning operation to cause the external device to execute the predetermined operation, and
    the control section causes the communication section to transmit the second data to the external device when, after the transmission of the first data is performed, the external device is actually controlled by the living body in an operating phase and the communication section receives the designation signal from the external device.

5. A method for controlling an internal device of a brain-machine interface system, the internal device adapted to be implanted in a living body, the method comprising:
    wirelessly transmitting first data corresponding to electroencephalogram signals of the living body for causing an external device to execute a predetermined operation which are detected through a group of N (N is 2 or more) electrodes to an external device at a communication rate which is lower than a value that is necessary for transmitting in real time;
    after the wireless transmission of the first data is performed, wirelessly receiving, from the external device, a designation signal designating a group of M electrode(s), M being smaller than N; and
    wirelessly transmitting second data corresponding to electroencephalogram signals of the living body for causing the external device to execute the predetermined operation which are detected through the group of M electrode(s) to the external device in real time.

6. The controlling method according to claim 5, further comprising:
    prior to the transmission of the first data, repeatedly storing in a storage section the first data.

7. The controlling method according to claim 5, further comprising:
    prior to the transmission of the first data, wirelessly transmitting a part of the first data to the external device.

8. The controlling method according to claim 5, wherein
    the first data is wirelessly transmitted to the external device when the living body performs a learning operation to cause the external device to execute the predetermined operation, and
    the designation signal is wirelessly received from the external device after the wireless transmission is performed and when the external device is actually controlled by the living body in an operating phase.

9. An internal device of a brain-machine interface system, the internal device adapted to be implanted in a living body, the internal device comprising:
    a data acquisition section;
    a communication section which wirelessly communicates with an external device; and
    a control section which controls the communication section, wherein
    the control section causes:
    the data acquisition section to acquire first data corresponding to electroencephalogram signals of the living body for causing the external device to execute a predetermined operation which are detected through N (N is 2 or more) electrodes, the first data having a first data amount;
    the communication section to transmit the first data to the external device at a communication rate which is lower than a value that is necessary for transmitting in real time;
    when, after the transmission is performed, the communication section receives, from the external device, a designation signal designating a second data amount which is smaller than the first data amount, the data acquisition section to acquire second data corresponding to electroencephalogram signals of the living body for causing the external device to execute the predetermined operation which are detected through the N electrodes, the second data having the second data amount; and the communication section to transmit the second data to the external device in real time.

10. The internal device according to claim 9, wherein the data acquisition section acquires the first data by sampling the electroencephalogram signals at a first sampling rate, and acquires the second data by sampling the electroencephalogram signals at a second sampling rate which is lower than the first sampling rate.

11. The internal device according to claim 9, wherein the data acquisition section acquires the first data by A/D-converting the electroencephalogram signals at a first resolution, and acquires the second data by A/D-converting the electroencephalogram signals at a second resolution which is lower than the first resolution.

12. A method for controlling an internal device of a brain-machine interface system, the internal device adapted to be implanted in a living body, the method comprising:

acquiring first data corresponding to electroencephalogram signals of the living body for causing an external device to execute a predetermined operation which are detected through a group of N (N is 2 or more) electrodes, the first data having a first data amount;

wirelessly transmitting the first data to an external device at a communication rate which is lower than a value that is necessary for transmitting in real time;

after the wireless transmission of the first data is performed, wirelessly receiving, from the external device, a designation signal designating a second data amount rather than the first data amount;

acquiring second data corresponding to electroencephalogram signals of the living body for causing the external device to execute the predetermined operation which are detected through the group of N electrodes, the second data having the second data amount; and wirelessly transmitting the second data to the external device in real time.

13. The controlling method according to claim 12, wherein the first data are acquired by sampling the electroencephalogram signals at a first sampling rate, and the second data are acquired by sampling the electroencephalogram signals at a second sampling rate which is lower than the first sampling rate.

14. The controlling method according to claim 12, wherein the first data are acquired by A/D-converting the electroencephalogram signals at a first resolution, and the second data are acquired by A/D-converting the electroencephalogram signals at a second resolution which is lower than the first resolution.

* * * * *